United States Patent [19]

Borody et al.

[11] Patent Number: 6,132,767
[45] Date of Patent: *Oct. 17, 2000

[54] ADMINISTERING OSMOTIC COLONIC EVACUANT CONTAINING A PICOSULFATE

[76] Inventors: Thomas Julius Borody; Walter George Shortis; Nicolas Peter Shortis, all of 144-Great North Rd., Five Dock N.S.W. 2046, Australia

[*] Notice: This patent is subject to a terminal disclaimer.

[21] Appl. No.: 09/148,857

[22] Filed: Sep. 8, 1998

Related U.S. Application Data

[63] Continuation of application No. 08/742,798, Oct. 31, 1996, Pat. No. 5,858,403.

[30] Foreign Application Priority Data

Nov. 3, 1995 [AU] Australia .................................. PN6345

[51] Int. Cl.$^7$ ...................................................... A61K 9/64
[52] U.S. Cl. ........................... 424/456; 424/451; 424/458; 424/463; 424/464; 424/489; 424/78.01; 424/709

[58] Field of Search ...................................... 424/451, 456, 424/458, 463, 464, 489, 78.01, 709

[56] References Cited

U.S. PATENT DOCUMENTS 5,616,346  4/1997  Aronchick ................................ 424/606
5,858,403  1/1999  Borody et al. ........................... 424/456

*Primary Examiner*—Jeffrey Stucker

[57] ABSTRACT

Colonic evacuation, treatment of small bowel bacterial overgrowth or irritable bowel syndrome or treating acute or chronic bacterial bowel infection comprises administering an osmotic colonic evacuant in solid form, preferably a mixture of sodium dihydrogen phosphate and disodium hydrogen phosphate or a sulfate based laxative comprising a picosulfate, together with a diluent.

13 Claims, No Drawings

ADMINISTERING OSMOTIC COLONIC EVACUANT CONTAINING A PICOSULFATE

CROSS-REFERENCE TO RELATED APPLICATION

This is a continuation of application Ser. No. 08/742,798, filed Oct. 31, 1996, now U.S. Pat. No. 5,858,403.

TECHNICAL FIELD

The present invention relates to orthostatic lavage solutions or colonic evacuants for cleansing the gastrointestinal tract, or for the treatment of bowel diseases and/or disorders.

BACKGROUND ART

The advent of colonoscopy brought with it the need for a simplified, routine bowel cleansing protocol or product to achieve a clean colonic mucosa required by the colonoscopist to detect even small lesions in the bowel, e.g. small polyps. Similar requirements exist for colonic surgery.

In the early days of colonoscopy, during the late 1970's, numerous protocols for bowel cleansing were designed by individual bowel surgeons and gastroenterologists to satisfy the requirements of their particular practices. Such protocols included the use of fasting in combination with various purgatives such as Epsom salts or osmotic agents plus enemas. Though, when complex protocols were followed strictly they often achieved their effect and resulted in a clean bowel. However, the protocols were invariably complex and required on average 3 days of cleansing which made them unpleasant and unacceptable. Furthermore, they were often dangerous because they caused marked fluid and electrolyte shifts in body compartments and on rare occasions predisposed to arrythmias, hypertension and in fact demise of the patient.

To overcome the problem of fluid shifts, Fordtrau developed an orthostatic lavage which combined with a large muscular, non-absorbable polyethylene glycol (PEG) compounded with a balanced electrolyte solution resembling concentrations found in the human serum. Such a lavage achieved very adequate levels of bowel cleansing, with minimal fluid and electrolyte shifts but at the expense of patient compliance and acceptability. PEG solutions produce volumogenic diarrhoea, by requiring ingestion of large volumes of the electrolyte solution. Finally 4 to 5 liters of the solution are required to obtain adequate cleansing for colonoscopy or bowel surgery. With such large volumes being drunk by the patient and with the taste of the electrolyte and PEG being particularly unpleasant, patients frequently experienced nausea, vomiting and bloating. Those requiring a colonoscopy on repeated occasions would clearly identify the PEG lavage as the most unpleasant aspect of colonoscopy. On occasions the level of discomfort caused by the cleansing lavage proved to be counter productive to reaching the desired aim of colonic cleansing, as patients would terminate ingesting the PEG solution, either due to the bad taste or nausea/vomiting.

It was for the above reasons that an effort was made to develop a favourable flavouring for the PEG lavage solution, and to reduce the need for large volume ingestion from 4 to 3 liters This was achieved by adding ascorbic acid, which acted as both a flavouring agent and a diarrheogenic compound reducing the volume required for ingestion from 4 to 3 liters. This improvement resulted in the Australian Patent No. 623,627 and equivalent US and European patents. Nevertheless, the still large volume of solution (3 liters) required to cleanse the bowel remained an obstacle to adequate cleansing in some patients.

As a result, there developed a shift back to osmotic diarrheogenic agents which required the patient to ingest a small volume of foul tasting electrolyte buffered solution (eg. phosphate based FLEET laxative) which would extract by osmotic tension a large volume of fluid from the patient's body and cause diarrhoea. There was therefore a clear advantage with this approach, since the patients did not need to keep on drinking a large volume of bad-tasting solution. However, osmotically active agents were notorious for causing electrolyte and fluid shifts, resulting in marked weight loss, hyperphosphataemnia and death in children, arrythmias and cardiac deaths in the more frail elderly patients. The side effects of nausea/vomiting continued to be a problem. To overcome the massive fluid shifts without the patient undergoing cleansing, the phosphate-based products were marketed to be combined with the ingestion of large volumes of pleasant-tasting glucose-free liquids such as water or mineral water. This exogenous input of a volume of water helped to effect fluid shifts. A portion of the fluid for the diarrheogenic effect originated in patients body fluids, while the remainder came from ungested water. Several trials covering palatability and effectiveness of the PEG versus Phosphate solutions, reached the conclusion that both can achieve comparable bowel cleansing and both continue to suffer from unpleasant taste and excessive volume.

Yet another problem to overcome has been the development of hyperphosphataemia and dehydration with potential of arrythmias and resulting syncope and reports of deaths—especially in children. With the small volume of the currently available phosphate-based evacuants, patients are able to drink simply the evacuant and not follow on with any further water. It would be therefore prudent to build in a safety system whereby numerous capsules will have to be swallowed with a fair volume of water to prevent the concentrating effect of the diarrhoea.

It would therefore be of advantage to develop a product which could be free of "foul tasting fluid" and yet achieve bowel cleansing while drinking acceptable amounts of liquids such as water, dietary soft drinks or mineral water.

A further problem which frequently presents itself during diagnostic colonoscopy is the foam-like bubbles which obstruct the viewing clarity, especially in the proximal colon. This foaming is a phenomenon caused by the rapid passage into the colon of bile secreted into the lumen of the bowel by the liver. In a proportion of patients, the caecum and especially the ascending colon are almost totally covered by a film of bile-containing foam, precluding a clear view of the mucosa. Such obstruction of view has on occasions led to a mis-diagnosis by the colonoscopist of colonic polyps and small cancers. Therefore there is a need to prevent foaming within the colon during the cleansing process. This has been attempted by injecting anti-foaming agents into the colon during colonoscopy. This method can achieve local de-foaming, but it is time consuming and rarely adequate. There is a need therefore to include an anti-foaming agent into the bowel-preparation formulation, to achieve uniform anti-foaming throughout the 1 meter length of the colon.

The objective of the present invention is to overcome the above-mentioned problems, of bad taste and foaming without sacrificing the excellent bowel-cleansing characteristics of the phosphate-based lavage solution. An added effect of adding an anti-foaming agent is the increase in lubrication of the colonic surface, thereby facilitating speed of colonoscopy to the caecum.

OBJECTS OF THE INVENTION

It is an object of the present invention to provide an osmotic colonic evacuant which does not cause arrythmia, dehydration, hypotension, marked electrolyte and fluid shifts, marked weight loss, cardiac deaths, nausea/vomiting or fainting when ingested by a patient. It is a further object of the present invention to provide a method of evacuating a patient's colon by administering a treatment regimen of an osmotic colonic evacuant and a diluent. Another object of the present invention is to provide a sequential pack for the oral administration of an osmotic colonic evacuant to a patient. It is a further object of the present invention to provide a method of treating small bowel bacterial overgrowth or irritable bowel syndrome in a patient. Another object of the present invention is to provide a method of treating acute or chronic bacterial bowel infection in a patient.

DISCLOSURE OF THE INVENTION

According to a first embodiment of the present invention there is provided an osmotic colonic evacuant in solid oral dosage form comprising an orthostatic lavage in powder form and a pharmaceutically acceptable excipient, diluent and/or adjuvant.

According to a second embodiment of the present invention there is provided a method of evacuating a patient's colon, comprising orally administering to said patient a treatment regimen of an osmotic colonic evacuant in powder form together with a diluent.

According to a third embodiment of the present invention there is provided a method of treating small bowel bacterial overgrowth or irritable bowel syndrome in a patient in need of such treatment, comprising administering to said patient a treatment regimen of an osmotic colonic evacuant in powder form together with a diluent.

According to a fourth embodiment of the present invention there is provided a method of treating acute or chronic bacterial bowel infection in a patient in need of such treatment, comprising administering to said patient a treatment regimen of an osmotic colonic evacuant in powder form together with a diluent.

According to a fifth embodiment of the present invention there is provided a sequential pack for the oral administration of at least two treatment regimens comprising a first treatment regimen comprising an osmotic colonic evacuant in solid oral dosage form. in unit dosage form adapted and presented for a first administration period, together with a second treatment regimen comprising an osmotic colonic evacuant in solid oral dosage form, in unit dosage form adapted and presented for a second administration period.

Generally the osmotic colonic evacuant is a phosphate based laxative, for example sodium dihydrogen phosphate, disodium hydrogen phosphate, sodium biphosphate. sodium acid pyrophosphate, or mixtures thereof; or a sulfate based laxative for example sodium picosulfate, sodium sulfate, magnesium sulfate or mixtures thereof. Typically the preferred colonic evacuant is a mixture of sodium dihydrogen phosphate and disodium hydrogen phosphate or a mixture of sodium picosulfate and magnesium oxide.

The colonic evacuant is a solid oral dosage form. Typically selected from a tablet for example a compressed tablet, a coated tablet and/or an exploding tablet; capsule for example a coated capsule and/or an exploding capsule; lozenge; pill or powder. Preferably the solid oral dosage form is coated to avoid dissolution in the mouth.

Typically the capsules or tablets may contain sodium starch glycollate, cross linked povidone or cross carmellose sodium to convert the capsules or tablets into exploding capsules or tablets.

Generally the diluent is any liquid suitable for ingestion. Preferably the diluent is water, mineral water, glucose-free mineral water, glucose-free cordial or glucose-free soft drink. The volume of diluent consumed with the osmotic colonic evacuant varies from 250 mL to 1500 mL, which is approximately one third the volume of diluents consumed with known colonic evacuants.

The amount of osmotic colonic evacuant administered to a patient is usually in the range of 1 mg to 200 g. When the osmotic colonic evacuant is a phosphate based laxative, the range is usually from 5 to 200 g, preferably 5 to 100 g, preferably 10 to 50 g, more preferably 20 to 30 g. Typically the phosphate based laxative contains 4.9 g disodium hydrogen phosphate and 24.7 g sodium dihydrogen phosphate. When the osmotic colonic evacuant is a sulfate based laxative, the range is usually from 1 to 100 mg, preferably 5 to 50 mg, preferably 5 to 25 mg, more preferably 10 mg.

Generally the osmotic colonic evacuant is orally administered to a patient over a period of time. The osmotic colonic evacuant is usually prepared as a number of tablets or capsules which are taken over a period of time.

A typical example of a treatment regimen of the invention using phosphate based laxatives involves the preparation of the colonic evacuant into approximately 25 tablets or capsules. Approximately 5 tablets or capsules are ingested with approximately one glass of diluent over a period of 1 second to 20 minutes, typically 5 seconds to 5 minutes. typically 10 seconds to 3 minutes, typically 30 seconds to 15 minutes, typically 15 minutes to 20 minutes, typically 1 minute to 10 minutes, more typically 1 minute to 6 minutes. A further 5 tablets or capsules are ingested with approximately one glass of diluent over 10 seconds to 20 minutes, typically 30 seconds to 15 minutes, or 15 minutes to 20 minutes, typically 1 minute to 10 minutes, more typically 1 minute to 6 minutes after approximately 20 minutes to 2.5 hours, typically 25 minutes to 1 hour, more typically 30 to 40 minutes. This regimen is repeated until all the tablets or capsules have been ingested.

A typical example of a treatment regimen of the invention using phosphate based laxatives involves the preparation of the colonic evacuant into approximately 5 to 20 tablets or capsules. Approximately one fifth of the tablets or capsules are ingested with approximately one glass of diluent over a period of 1 second to 20 minutes, typically 5 seconds to 5 minutes, typically 10 seconds to 3 minutes, typically 30 seconds to 15 minutes, typically 15 minutes to 20 minutes, typically 1 minute to 10 minutes, more typically 1 minute to 6 minutes. A further one fifth of the tablets or capsules are ingested with approximately one glass of diluent over 10 seconds to 20 minutes, typically 30 seconds to 15 minutes, or 15 minutes to 20 minutes, typically 1 minute to 10 minutes. more typically 1 minute to 6 minutes after approximately 20 minutes to 2.5 hours, typically 25 minutes to 1 hour, more typically 30 to 40 minutes. This regimen is repeated until all the tablets or capsules have been ingested.

Generally the typical examples of the treatment regimen take 2 to 12 hours, preferably 2.5 to 6.5 hours, more preferably 2 to 4.5 hours, even more typically 2 to 3.5 hours.

If the treatment regimen is administered in two parts, there is usually a difference of 4 to 16 hours, typically 4 to 12 hours, preferably 4 to 8 hours, more preferably 4 to 6 hours, between the administration of the first treatment regimen and the administration of the second treatment regimen.

The osmotic colonic evacuant of the present invention may further comprise an anti-foaming or lubricating agent or antiflatulent, for example simethicone, activated charcoal. The amount of anti-foaming or lubricating agent or antiflatulent used in the osmotic colonic evacuant ranges from 1 to 500 mg, preferably 5 to 300 mg, more preferably 50 to 200 mg, more preferably 75 to 150 mg. Typically 100 mg simethicone is used in the osmotic colonic evacuant of the invention.

The osmotic colonic evacuant of the present invention may further comprise an antacid. Examples of antacids include magnesium oxide, calcium carbonate, magnesium alginate, magnesium hydroxide, magnesium carbonate, magnesium citrate, magnesium aspartate, magnesium trisilicate. The amount of antacid used in the osmotic colonic evacuant ranges from 0.5 to 50 g, preferably 1 to 30 g, preferably 1 to 20 g, more preferably 2 to 16 g. Typically 3.5 g of magnesium oxide is used in the osmotic colonic evacuant of the invention, alternatively 7.5 g magnesium carbonate or 15.5 g magnesium citrate is used in the osmotic colonic evacuant of the invention.

The osmotic colonic evacuant of the present invention may further comprise ascorbic acid. The amount of ascorbic acid used in the osmotic colonic evacuant of the present invention ranges from 0.5 to 100g, preferably 1 to 50 g, preferably 1 to 25 g, more preferably 5 to 15 g, more preferably 12 or 14 g. The ascorbic acid may be coated with silicone or ethyl cellulose.

The osmotic colonic evacuant of the present invention are also useful in the treatment of certain gastrointestinal conditions such as small bowel bacterial overgrowth and irritable bowel syndrome as well as useful in treating acute or chronic bacterial bowel infections, for example, infection of the bowel with one or more bacteria including *Campylobacter jejuni, Yersinia enterocolitica, Clostridium difficile, Cryptosporidium isospora belli*. The osmotic colonic evacuant of the present invention can also be used in the treatment of fungal or viral infections in the bowel. The osmotic colonic evacuant of the present invention can also be used in the treatment of chronic inflammatory bowel disease such as Crohn's disease or ulcerative colitis.

BEST MODE FOR CARRYING OUT THE INVENTION

The present invention provides a formulation of an osmotic colonic evacuant in a powder, whose volume is small enough to place in capsules. This is then ingested with water, or other acceptable fluid, e.g. dietary water-based drinks such as diet soft drinks, cordials, mineral water. An adequate volume of fluids needs to be ingested by the patient to minimize osmotic diarrhoea by providing the necessary fluid volume to the body. This prevents dangerous electrolyte and fluid shifts. The invention also describes the addition to the formulation of an anti-foaming lubricating agent, to facilitate mucosal visibility in the colon.

The invention describes a powder formulation of reduced ingredients, which can be encapsulated in small enough numbers of capsules to be clinically useful. The capsules house the "foul-tasting" compound which are thereby delivered to the stomach and small bowel without having to be dissolved in water for ingestion. The patient therefore does not taste the compound. Normally the formulation required all ingredients which are too voluminous in powdered form to be placed in capsules. The current reformulation allows for a reduced volume of powder which, when housed in capsules, still results in a small enough number of capsules to be acceptable to most patients to ingest.

The formulation includes either:

| Ingredient | Range | Best form |
|---|---|---|
| sodium dihydrogen phosphate (monohydrate) | 5 to 200 g | 24.7 g |
| disodium hydrogen phosphate (anhydrous) | 1 to 50 g | 4.9 g |
| with or without simethicone | 5 to 300 mg | 100 mg |
| or | | |
| sodium picosulfate | 1 to 100 mg | 10 mg |
| magnesium oxide | 1 to 30 g | 3.5 g |
| citric acid (anhydrous) | 1 to 50 g | 12 g |
| with or without simethicone | 5 to 300 mg | 100 mg |
| or | | |
| sodium picosulfate | 1 to 100 mg | 10 mg |
| magnesium oxide | 1 to 30 g | 3.5 g |
| ascorbic acid (anhydrous) | 1 to 50 g | 12 g |
| with or without simethicone | 5 to 300 mg | 100 mg |
| or | | |
| sodium picosulfate | 1 to 100 mg | 10 mg |
| magnesium carbonate (pond) | 1 to 30 g | 7.5 g |
| citric acid | 1 to 50 g | 14 g |
| with or without simethicone | 5 to 300 mg | 100 mg |
| or | | |
| sodium picosulfate | 1 to 100 mg | 10 mg |
| magnesium citrate | 1 to 50 g | 15.5 g |
| with or without simethicone | 5 to 300 mg | 100 mg |

The above powder can be:
i. Encapsulated, typically resulting in around 25 capsules. However, depending on compression of powders, size of capsules and method of administration the formulation may result in 7 to 60 capsules.
ii. Compressed in tablet form—which may be coated by a film to avoid dissolution in the mouth. High compression can achieve even a smaller number of tablets, e.g. 5 to 20 tablets.
iii. Packaged in sachets for dissolution and ingestion in liquid form.

The formulation is administered in such a way as to maximize compliance—in the typical encapsulated form of 25 capsules, one fifth (5 capsules) of the capsules are ingested with each of five standard glasses of water, glucose-free cordial, or glucose-free soft drink. The frequency of ingestion can vary, but typically should take place every 20 minutes to 2.5 hours, typically 25 minutes to 1 hour, more typically 30 to 40 minutes. The whole procedure can be given twice in one day, especially in patients with stubborn constipation.

Generally the procedure takes from 2 to 12 hours, preferably 2.5 to 6.5 hours, more preferably 2 to 4.5 hours, even more typically 2 to 3.5 hours. However if the formulation is administered in two parts, there is a difference of 4 to 12 hours, typically 4 to 12 hours, preferably 4 to 8 hours, more preferably 4 to 6 hours, between the administration of the first treatment regimen and the administration of the second treatment regimen.

The capsules can also be used as a laxative, but at all times with added fluid, as a longer term basis, e.g. daily or second-daily, in various forms of constipation.

EXAMPLE 1

In a 48 year old female patient who had previously taken PEG-balanced salt solution and on a second occasion a Fleet oral phosphate laxative both resulting in severe nausea. bloating and vomiting—or the third colonoscopic examination the patient was given 25 capsules of the current formulation. She progressively ingested 5 capsules with a glass of mineral water or "Diet Coke". This resulted in bowel evacuation one and a half hours later and in on-going diarrhoeal stools for the next 5 to 7 hours. The final stools were clear of faecal fragments. At colonoscopy a clear view to the caecum was obtained and an appendiceal luminal mass identified. No evidence of foaming appeared.

EXAMPLE 2

A 27 year old male patient returned from a holiday trip in Bangkok and complained of abdominal cramping and marked diarrhoea. He was quite anorexic and in quite severe pain. He was advised to ingest 20 capsules of a combination of sodium acid phosphate and sodium phosphate followed by 6 glasses of water. After experiencing profuse diarrhoea the abdominal symptoms were completely relieved within 4 hours. Cramping and anorexia disappeared and by the evening the patient was able to ingest a meal feeling quite hungry. The condition did not recur.

EXAMPLE 3

A 51 year old male who on previous colonoscopy had abundance of bile product obscuring total view of the ascending colon was given 25 capsules of a combination of sodium picosulfate, magnesium oxide and citric acid at 12 pm and 6 pm on the day prior to colonoscopy. After the 6 pm ingestion and at 8 am on the examination day he was given 200 mg dose of simethicone. The endoscopist was able to reach the caecum without obstructed view. A polyp was sighted and removed.

INDUSTRIAL APPLICABILITY

The osmotic colonic evacuant of the present invention requires a smaller volume of diluent and is thus a safer alternative to the colonic evacuants on the market because the incidence of arrythmia, dehydration, hypotension, marked electrolyte and fluid shifts. marked weight loss, cardiac deaths, nausea/vomiting or fainting is greatly reduced in a patient.

We claim:

1. A method of evacuating a patient's colon, comprising orally administering to said patient a treatment regimen of an osmotic colonic evacuant in solid form together with a diluent of volume of at least 500 ml, wherein said colonic evacuant comprises a sulfate based laxative comprising a picosulfate, without administration of a polyethylene glycol electrolyte lavage solution.

2. The method of claim 1, wherein the osmotic colonic evacuant further comprises an antacid.

3. The method of claim 1, wherein the osmotic colonic evacuant further comprises citric acid.

4. The method of claim 1, wherein the osmotic colonic evacuant further comprises ascorbic acid.

5. The method of claim 1, wherein the osmotic colonic evacuant further comprises an anti-foaming or lubricating agent.

6. The method of claim 1, wherein the diluent is a glucose-free diluent.

7. The method of claim 1, wherein the treatment regimen comprises administering a solid oral dosage form of osmotic colonic evacuant together with a diluent every 30 to 40 minutes for an administration period of 2.5 to 12 hours.

8. A method of treating small bowel bacterial overgrowth or irritable bowl syndrome in a patient in need of such treatment, comprising administering to said patient a treatment regimen of an osmotic colonic evacuant in solid form together with a diluent of volume of at least 500 ml, wherein said colonic evacuant comprises a sulfate based laxative comprising a picosulfate.

9. The method of claim 8, wherein the diluent is a glucose-free diluent.

10. The method of claim 8, wherein the treatment regimen comprises administering a solid oral dosage form of osmotic colonic evacuant together with a diluent every 30 to 40 minutes for an administration period of 2.5 to 12 hours.

11. A method of treating acute or chronic bacterial bowel infection in a patient in need of such treatment, comprising administering to said patient a treatment regimen of an osmotic colonic evacuant in solid form together with a diluent of volume of at least 500 ml, wherein said colonic evacuant comprises a sulfate based laxative comprising a picosulfate.

12. The method of claim 11, wherein the diluent is a glucose-free diluent.

13. The method of claim 11, wherein the treatment regimen comprises administering a solid oral dosage form of osmotic colonic evacuant together with a diluent every 30 to 40 minutes for an administration period of 2.5 to 12 hours.

* * * * *